United States Patent [19]

Barba

[11] 4,001,002
[45] Jan. 4, 1977

[54] METHOD OF PROMOTING FLOWERING IN FRUIT PLANTS

[76] Inventor: Ramon C. Barba, 428 Anos St., Los Banos, Laguna, Philippines

[22] Filed: Sept. 11, 1974

[21] Appl. No.: 504,948

[30] Foreign Application Priority Data

July 3, 1974 Philippines ............................ 16014

[52] U.S. Cl. ........................................ 71/65; 71/90; 71/99; 71/104; 71/114; 71/117
[51] Int. Cl.² ............................................ A01N 5/00
[58] Field of Search ................................... 71/65, 99

[56] References Cited

UNITED STATES PATENTS

| | | |
|---|---|---|
| 2,051,460 | 8/1936 | von Skrbensky ...................... 71/65 |
| 2,213,809 | 9/1940 | Dustman ............................... 71/65 |
| 2,258,291 | 10/1941 | Jones ..................................... 71/65 |
| 2,258,292 | 10/1941 | Jones ..................................... 71/65 |

*Primary Examiner*—Joseph Paul Brust
*Attorney, Agent, or Firm*—Sughrue, Rothwell, Mion, Zinn & Macpeak

[57] ABSTRACT

The objectives and merits of this invention reside in the specific use of certain chemicals to regulate the flowering of fruit plants, such as the mango and pineapple.

12 Claims, No Drawings

METHOD OF PROMOTING FLOWERING IN FRUIT PLANTS

BACKGROUND OF THE INVENTION

As far as is known, the compounds of this invention have never been used, prior to this invention, directly as active components for flower induction. Such chemicals are manufactured and sold for different purposes.

Mango flowering is seasonal, normally occuring in the Philippines between December to March, depending on the location. Flower control is desirable to produce out of season crop as well as to increase production during the normal flowering season or to offset the common biennial bearing habit. Smudging or smoking to promote flowering is costly, laborious and unreliable. Attempts have been made by other researchers to promote flowering with growth regulators and some degree of success has been obtained with ethrel, a compound that produces ethylene in the plant. A method that is less costly, more effective and consistent is desirable. The discovery of methods using compounds that satisfy these criteria are part of the present invention.

In pineapple, regulation of flowering is likewise important to produce out of season crop and to time fruiting for specific harvest dates. Uniform maturity facilitates harvesting and other plantation operations. Although several compounds are known to be effective for pineapple flowering, unlike the mango, a cheaper and more effective method is still desirable.

It is the primary objective of this invention ot provide a method of promoting flowering of fruit plants, such as the mango and pineapple using certain chemicals hereinafter described.

Further, it is an object of the present invention to provide a method of promoting flowering of fruit plants, such as the mango and pineapple, that are of flowering age.

SUMMARY OF THE INVENTION

The present invention provides an aqueous solution of nitrate compounds such as ammonium nitrate, potassium nitrate, sodium nitrate, calcium nitrate, magnesium nitrate, barium nitrate and nitric acid; thiocyanate compounds such as ammonium thiocyanate, potassium thiocyanate, sodium thiocyanate, calcium thiocyanate, magnesium thiocyanate, barium thiocyanate; or thioureas such as ethylene thiourea and thiourea, and mixtures thereof, which when sprayed to fruit plants, such as the mango and pineapple, induces flowering. The nitrate compound can be used in a concentration of 0.2–3.0%; the thiocyanate compound can be used in a concentration of 0.1–1.5%; and the thiourea compound can be used in a concentration of 0.2–3.0%.

DETAILED DESCRIPTION OF THE INVENTION

The present invention can best be understood by way of examples as follows:

EXAMPLE I

When separate aqueous solutions of potassium nitrate, ammonium nitrate, sodium nitrate, calcium nitrate, magnesium nitrate, barium nitrate and nitric acid were sprayed in December to wet the leaves of mature mango plants with dormant leaves and buds, flowering was promoted between 7 and 21 days. Flowering was also improved based on size and number of inflorscence when used during the normal flowering season in the experimental area in February to March. Flowering was also induced at different time of the year on bearing trees with fully mature and dormant leaves and buds. Flower induction was easier when approaching the normal flowering season at which time lower concentrations of the solution were found effective.

The same solutions were found effective in promoting flowering of pineapple when sprayed to the whole plant or when poured to the growing point, or heart, at 10 to 100 ml per plant.

The compounds were effective at an average rate of 0.5 to 2.0 percent in water. Though effective, lower concentrations were weaker and higher concentrations may cause leaf burn.

EXAMPLE II

Potassium nitrate at 0.25 to 2.0 percent concentration in water when sprayed to mature and dormant mango plants in December promoted flowering between 7 and 21 days, usually within 10 days. Untreated plants did not flower until the following February to March. The results were confirmed on a larger scale using 100 trees.

The same solution when applied as spray to pineapple or poured to the heart at 10 to 100 ml per plant, promoted flowering of 15 month old plants. Flowering was observed 70 to 90 days following treatment in September at which time untreated plants did not yet flower.

Separate aqueous solutions of sodium nitrate, potassium nitrate, ammonium nitrate, calcium nitrate, magnesium nitrate, barium nitrate and nitric acid, when applied in the same manner and condition as described for potassium nitrate, were effective in promoting flowering of the mango and pineapple. They were somewhat less effective than potassium nitrate.

EXAMPLE III

It was determined that the nitrate molecule is the effective component of these compounds for mango and pineapple flowering. Other inorganic salts of sodium, potassium, ammonium, calcium and magnesium such as sulfate, chloride, phosphate and carbonate were found ineffective. The discovery therefore points to the method of promoting flowering with nitrate compounds.

EXAMPLE IV

Mixture of two or more of the chemicals above were found effective in promoting flowering of mango and pineapple when used as described for potassium nitrate between 0.25 and 2.0 percent total concentration in water.

EXAMPLE V

When separate aqueous solutions of potassium thiocyanate, ammonium thiocyanate, sodium thiocyanate, calcium thiocyanate, magnesium thiocyanate and barium thiocyanate wre sprayed to wet the leaves of mature mango plants with dormant leaves and buds in December, flowering was promoted after 7 to 21 days, usually about 10 days, whereas untreated plants did not flower until February to March. The spray also improved flowering during the normal flowering period based on total number and length of inflorescence.

The same aqueous solution applied as spray or when poured to the heart promoted flowering of 15 month old pineapple plants between 70 to 90 days following treatment in September at which time untreated plants did not yet flower.

The thiocyanates were found effective up to 1.5 percent concentration but causes leaf burn with pineapple so that 1.0 percent or less is recommended.

EXAMPLE VI

It was shown that the thiocyanate molecule is the active component in promoting flowering among the compounds stated. Other compounds of sodium, potassium, ammonium, calcium, magnesium such as phosphate, thiosulfate, chloride, sulfate were found ineffective. The discovery therefore points to the method of promoting flowering with thiocyanate compounds as in the case of the nitrates.

EXAMPLE VII

Mixture of two or more of the thiocyanate compounds stated above were effective for mango and pineapple flowering if used as stated provided that the total aggregate concentration is within the effective concentration of each of the compounds mixed when used separately.

EXAMPLE VIII

An aqueous solution of thiourea and ethylene thiourea at 0.5 to 3.0 percent concentration, preferably 1.0 percent, when applied in the same manner and conditions as described for the thiocyanates and nitrates described above promoted flowering of mango and pineapple.

EXAMPLE IX

A mixture of thiourea and ethylene thiourea at a total concentration of 0.5 to 3.0 percent in water was found effective in forcing flowering of mango and pineapple when used as described.

EXAMPLE X

Any of the nitrates, thiocyanates and thioureas described were found effective in promoting flowering of the mango and pineapple when mixed in any number or sequence in an aqueous solution provided that the total aggregate concentration of the active compounds is not lower than the effective concentration of each component.

EXAMPLE XI

Addition of sodium naphthalene acetate and naphthalene acetic acid up to 0.1 percent, 2,4-dichlorophenoxyacetic acid up to 0.05 percent, ethrel up to 0.5 percent of the final solution improved the effects of the chemicals stated when used to promote flowering of the mango and pineapple.

EXAMPLE XII

Addition or mixture of water soluble fertilizers or foliar fertilizers containing nitrogen, phosphorus, potassium and trace elements improved the effect of any of the active compounds for mango and pineapple flowering.

Any of the solutions were found compatible when mixed with common insecticides and fungicides.

EXAMPLE XIII

On a limited scale, the aqueous solutions described were found effective in promoting flowering of other fruit plants such as *Eugenia cuminii, Citrus mitis, Sandoricum koetjape* and cashew.

What is claimed is:

1. A method of inducing flowering in a fruit plant which comprises applying a flowering inducing amount of potassium nitrate, sodium nitrate, calcium nitrate, magnesium nitrate, barium nitrate, ammonium nitrate or nitric acid to a fruit plant.

2. The method of claim 1 wherein the compound is applied as an aqueous solution thereof.

3. The method of claim 1 wherein the concentration of the chemical is between 0.2 to 3.0 percent in water.

4. The method of claim 1 wherein the compound is applied to the leaves and buds of the mango plant.

5. The method of claim 1 wherein the compound is applied to the leaves or the growing point of the pineapple plant.

6. The method of claim 3 in which the compound is ammonium nitrate.

7. The method of claim 3 in which the compound is potassium nitrate.

8. The method of claim 3 in which the compound is sodium nitrate.

9. The method of claim 3 in which the compound is calcium nitrate.

10. The method of claim 3 in which the compound is magnesium nitrate.

11. The method of claim 3 in which the compound is barium nitrate.

12. The method of claim 3 in which the compound is nitric acid.

* * * * *